(12) United States Patent
Brauers et al.

(10) Patent No.: US 9,788,791 B2
(45) Date of Patent: Oct. 17, 2017

(54) PATIENT MONITORING SYSTEM AND METHOD

(75) Inventors: Andreas Brauers, Aachen (DE); Olaf Such, Aachen (DE); Jens Muehlsteff, Aachen (DE); Harald Reiter, Aachen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1641 days.

(21) Appl. No.: 11/915,751

(22) PCT Filed: Jun. 1, 2006

(86) PCT No.: PCT/IB2006/051753
§ 371 (c)(1),
(2), (4) Date: Nov. 28, 2007

(87) PCT Pub. No.: WO2006/131855
PCT Pub. Date: Dec. 14, 2006

(65) Prior Publication Data
US 2008/0208063 A1    Aug. 28, 2008

(30) Foreign Application Priority Data
Jun. 7, 2005 (EP) .................... 05104933

(51) Int. Cl.
*A61B 5/08* (2006.01)
*A61B 5/00* (2006.01)
(Continued)

(52) U.S. Cl.
CPC ........ *A61B 5/6892* (2013.01); *A61B 5/04085* (2013.01); *A61B 5/113* (2013.01);
(Continued)

(58) Field of Classification Search
CPC ... A61B 5/6892; A61B 5/113; A61B 5/04085; A61B 2562/182; A61B 2562/0209; A61B 2562/046
(Continued)

(56) References Cited

U.S. PATENT DOCUMENTS 4,474,185 A * 10/1984 Diamond ................. 600/535
4,757,825 A * 7/1988 Diamond ............... A61B 5/11
340/575

(Continued)

FOREIGN PATENT DOCUMENTS

EP    0714629 A1    5/1996
EP    1211633 A1    6/2002
(Continued)

OTHER PUBLICATIONS

W. Q. Yang et al., "New AC-based capacitance tomography system" IEE Proc.-Sci. Meas. Technol., vol. 146, No. 1, Jan. 1999.*
(Continued)

*Primary Examiner* — Tiffany Weston
*Assistant Examiner* — Tho Tran

(57) ABSTRACT

The present invention relates to a patient monitoring system for monitoring cardio pulmonary performance or the like by means of capacitive measurement. Further the invention relates to a method for monitoring cardio pulmonary performance or the like by means of a capacitive measurement. In order to provide a reliable technique for monitoring cardio pulmonary performance or the like, which technique is particularly suitable for home use, a patient monitoring system (1) for monitoring cardio pulmonary performance or the like by means of capacitive measurement is suggested, said system (1) comprising a number of electrodes (2) arranged in the form of a matrix (3), said electrodes (2) being adapted to be integrated with a bed (4) or the like, each
(Continued)

Figure 1:
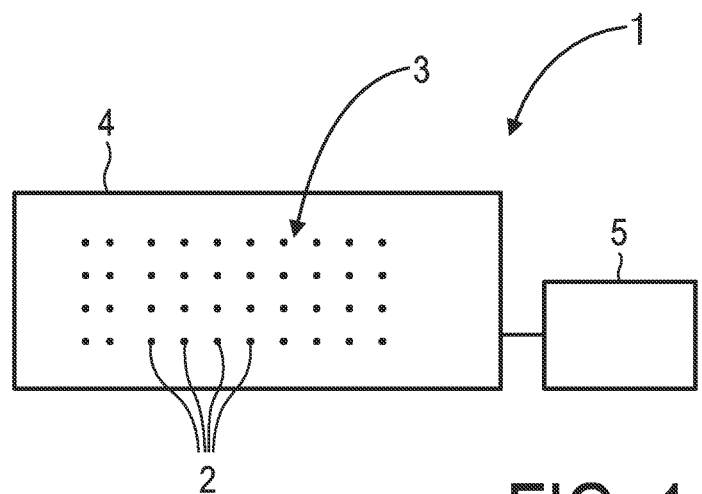

electrode (2) being individually selectable, means (5) for determining a number of electrodes (2) depending on the position of the patient on the bed (4) or the like, said means (5) being adapted to determine the number of electrodes (2) by determining the capacitance of a number of electrodes (2), and means (5) for selecting a number of said determined electrodes (2) for carrying out a capacitive measurement.

17 Claims, 2 Drawing Sheets

(51) Int. Cl.
    *A61B 5/0408*     (2006.01)
    *A61B 5/113*     (2006.01)

(52) U.S. Cl.
    CPC . *A61B 2562/0209* (2013.01); *A61B 2562/046* (2013.01); *A61B 2562/182* (2013.01)

(58) Field of Classification Search
    USPC .............. 600/484, 535, 587, 534, 393, 595; 434/247
    See application file for complete search history.

(56) References Cited

U.S. PATENT DOCUMENTS

| | | | | |
|---|---|---|---|---|
| 4,827,763 | A | * | 5/1989 | Bourland et al. ............... 73/172 |
| 5,010,772 | A | | 4/1991 | Bourland et al. |
| 5,196,008 | A | * | 3/1993 | Kuenecke et al. ............. 606/35 |
| 5,449,002 | A | | 9/1995 | Goldman ...................... 600/592 |
| 6,280,392 | B1 | * | 8/2001 | Yoshimi et al. .............. 600/534 |
| 6,450,957 | B1 | | 9/2002 | Yoshimi et al. |
| 6,454,705 | B1 | | 9/2002 | Cosentino et al. |
| 6,932,774 | B2 | * | 8/2005 | Nakatani et al. ............. 600/534 |
| 7,146,219 | B2 | * | 12/2006 | Sieracki et al. ................ 607/46 |
| 7,641,618 | B2 | * | 1/2010 | Noda et al. ................... 600/535 |
| 7,935,061 | B1 | * | 5/2011 | Breed et al. .................. 600/485 |
| 2001/0020395 | A1 | | 9/2001 | Hubbard |
| 2002/0070866 | A1 | | 6/2002 | Newham |
| 2003/0038949 | A1 | * | 2/2003 | Degertekin .......... G01B 11/026 356/498 |
| 2004/0010202 | A1 | | 1/2004 | Nakatani et al. |
| 2005/0054941 | A1 | | 3/2005 | Ting et al. |
| 2005/0107722 | A1 | * | 5/2005 | Ozaki et al. .................. 600/587 |
| 2006/0092032 | A1 | * | 5/2006 | Manlove ................ G01L 1/144 340/667 |

FOREIGN PATENT DOCUMENTS

| | | |
|---|---|---|
| JP | 62164435 A | 7/1987 |
| JP | 0248252 B2 | 10/1990 |
| JP | 0838437 A | 2/1996 |
| JP | 1014889 A | 1/1998 |
| JP | 2001037742 A | 2/2001 |
| JP | 2001299712 A | 10/2001 |
| JP | 2001340318 A | 12/2001 |
| JP | 2004024684 A | 1/2004 |
| JP | 2004024685 A | 1/2004 |
| WO | 02068921 A2 | 9/2002 |

OTHER PUBLICATIONS

Ishijima, "Cardiopulmonary Monitoring by Textile Electrodes Without Subject-Awareness of Being Monitored", Medical and Biological Engineering and Computing, vol. 35, No. 6, 1997, p. 685-690.

* cited by examiner

PATIENT MONITORING SYSTEM AND METHOD

The present invention relates to a patient monitoring system for monitoring cardio pulmonary performance or the like by means of capacitive measurement. Further the invention relates to a method for monitoring cardio pulmonary performance or the like by means of a capacitive measurement.

Bedside monitoring of parameters for patients with cardiac diseases is standard in hospital settings. There are also first approaches to measure cardio data or pulmonary data in a home environment. To make such a home monitoring system most unobtrusive, sensors which do not rely on a direct skin contact appear most attractive. Thus, capacitive sensing methods are most suitably to be used with such a system.

Capacitive sensing of bio signals inherently relies on the capacitive coupling of the "body electrode" to the sensing capacitance. This coupling may vary depending on the patient's motion, sweat on the patient's skin and intimacy of the contact or distance of the body to the sensing electrode. Additionally, non-contact sensing is vulnerable to parasitic signals, which do not come from the patient's body.

It is an object of the present invention to provide a reliable technique for monitoring cardio pulmonary performance or the like, which is particularly suitable for home use.

This object is achieved according to the invention by a patient monitoring system for monitoring cardio pulmonary performance or the like by means of capacitive measurement, said system comprising a number of electrodes arranged in the form of a matrix, said electrodes being adapted to be integrated with a bed or the like, each electrode being individually selectable, means for determining a number of electrodes depending on the position of the patient on the bed or the like, said means being adapted to determine the number of electrodes by determining the capacitance of a number of electrodes, and means for selecting a number of said determined electrodes for carrying out a capacitive measurement.

The object of the present invention is also achieved by a method for monitoring cardio pulmonary performance or the like by means of a capacitive measurement, which method comprises the steps of arranging a number of electrodes in the form of a matrix, which electrodes are adapted to be integrated with a bed or the like, each electrode being individually selectable, determining a number of electrodes depending on the position of the patient on the bed or the like, which determining of electrodes is performed by determining the capacitance of a number of electrodes and selecting a number of said determined electrodes for carrying out a capacitive measurement.

A basic idea of the present invention is to utilize a capacitive sensing concept using not only three or four separate electrodes, but an electrode matrix comprising a larger number of electrodes arranged adjacent to each other. These electrodes are adapted in a way that they can be integrated with a bed or the like, e.g. as a textile bed sheet or a sleeping pad or mattress. In other words, it is not necessary to position the patient exactly in a certain "measuring position". Instead the patient may position himself-herself in an arbitrary way.

Since in most cases the patient covers several electrodes within the electrode matrix, it is now necessary to find and select a number of measuring electrodes, i.e. electrodes which are most suitable to finally perform the capacitive measurement. To select those electrodes, the invention suggests to test the suitability of the electrodes with respect to the upcoming measurements before these measurements start.

A bed according to the present invention is defined as a surface or any other device to rest on or to sit on etc., e.g. a conventional bed, a hospital bed, a couch, a conventional chair, a dentist's chair, a wheelchair, an (operating) table, etc.

The suggested system and method can be used e.g. for ECG/heart rate signal detection, EEG, EMG, bio-impedance measurements, e.g. bio-impedance tomography, and similar measurements.

These and other aspects of the invention will be further elaborated on the basis of the following embodiments which are defined in the dependent claims.

According to a preferred embodiment of the invention, the system comprises a dielectric, said dielectric being of elastic constitution. As a dielectric any suitable kind of material may be used, e.g. a textile bed sheet or the like. The system further comprises a number of electrode pairs, in which each electrode pair is formed by a counter electrode positioned on the side of the dielectric that faces the patient, and a sensing electrode, which sensing electrode is positioned on the opposite side of the dielectric, and means for determining the capacitance of a number of electrode pairs. If the dielectric is arranged in a way that it is stressed by the patient if the patient is situated on the bed or the like, the changes in capacitance of the electrode pair, which depends on the position of the patient, can be determined. If the patient pushes down an upper electrode of an electrode pair, the dielectric will be compressed and the distance between the upper and the lower electrode will decrease. Thus the capacitance will increase. The increase of the capacitance can easily be detected by e.g. a simple bridge circuit.

Instead of using counter electrodes, as described above, in another preferred embodiment of the invention, the body of the patient is used as a "counter electrode".

According to this embodiment the system comprises a dielectric positioned adjacent to the number of electrodes in a way that it faces the patient if the patient is situated on the bed or the like. The patient now pushes down the dielectric directly, leading to an increase of the capacitance, which again can easily be detected by e.g. a simple bridge circuit.

In both cases electrodes with a high capacitance will be most suitable for carrying out the real measurement and will therefore be (pre)selected.

In another embodiment of the invention the electrodes are actively probed by supplying a voltage signal to a number of first electrodes, and determining an induced charge at a number of second electrodes. Adjacent electrodes are preferably used as first and second electrodes. Since the capacitance depends on the distance between an electrode and the patient's body, electrodes with a high signal coupling will be most suitable for carrying out the real measurement and will be (pre)selected.

In yet another embodiment of the invention the system comprises a shielding between the patient and the number of electrodes or between the patient and the dielectric. With the shielding it will be ensured, that only signals are detected that belong to immediate surroundings of said electrode.

If suitable electrodes have been (pre)selected, i.e. electrodes which show a high capacitance and/or a high signal coupling, the real measurement, e.g. measuring heart rate signals, is performed using said electrodes. The process of selecting suitable electrodes may include a preselection (according to the parameters described above) as well as a final selection, preferably taking into account the kind of measurement. For example, if an ECG measurement is to be carried out, the electrodes to be finally selected need to have a certain mutual distance.

For preselecting and/or finally selecting electrodes an analyzing unit is preferably used, which analyzing unit comprises a computer adapted to execute a computer program, which computer program comprises computer instructions to analyze input values (e.g. capacitance values and/or signal coupling values) and to find the most suitable electrodes for a certain kind of measurement for a certain position of the patient on the bed or the like. Additionally, the validity of measuring values can be evaluated. The object of the present invention is thus also achieved by a computer program, when the computer program is executed in a computer. The technical effects necessary according to the invention can thus be realized on the basis of the instructions of the computer program in accordance with the invention. Such a computer program can be stored on a carrier such as a CD-ROM or it can be available over the internet or another computer network. Prior to execution the computer program is loaded into the computer by reading the computer program from the carrier, for example by means of a CD-ROM player, or from the internet, and storing it in the memory of the computer. The computer includes inter alia a central processor unit (CPU), a bus system, memory means, e. g. RAM or ROM, storage means, e. g. floppy disk or hard disk units and input/output units.

Figure 2:
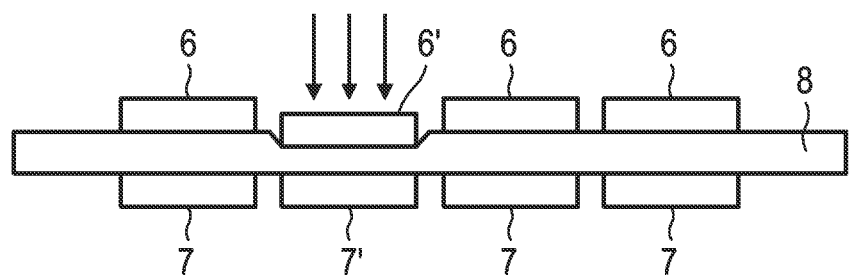
Figure 3:
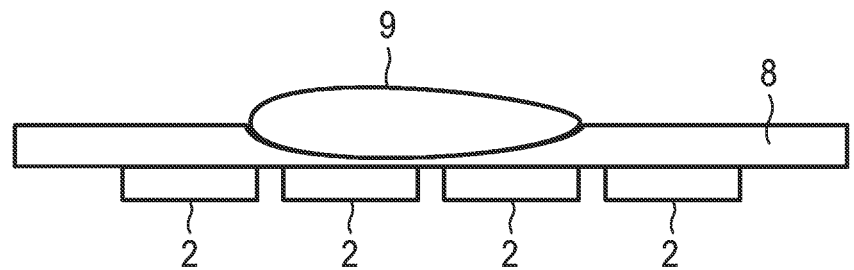
Figure 4:
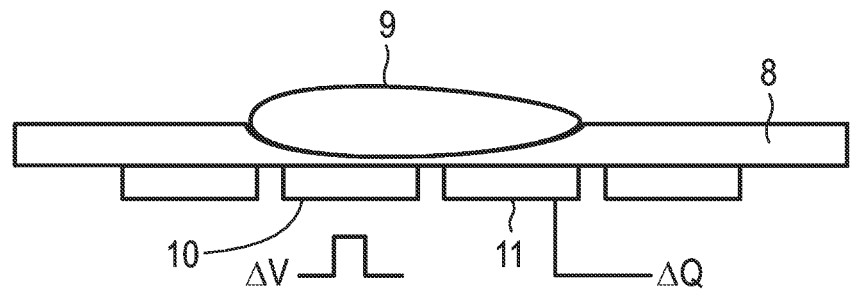
Figure 5:
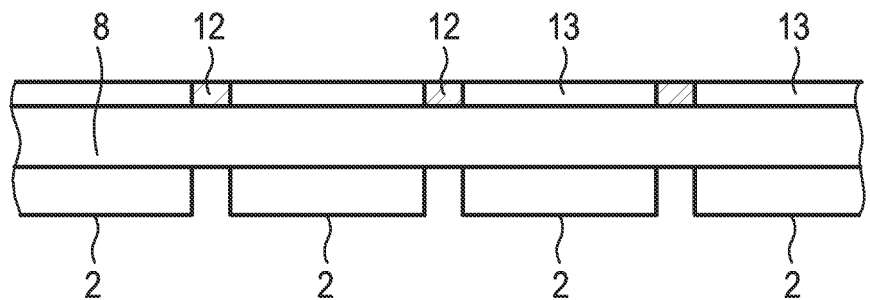

These and other aspects of the invention will be described in detail hereinafter, by way of example, with reference to the following embodiments and the accompanying drawings; in which FIG. 1 is a schematic top view showing a patient monitoring system according to the invention, FIG. 2 shows a position sensing using capacitive measurement with counter electrodes, FIG. 3 shows the principle of measurement using capacitive electrodes without counter electrodes, FIG. 4 shows the principle of measurement using capacitive electrodes without counter electrodes and with an active circuit, and FIG. 5 illustrates a capacitive structure with shielding.

The patient monitoring system 1 according to the present invention is adapted for an ECG measurement by means of capacitive measurement. As illustrated in FIG. 1, the system 1 comprises a number of capacitive non-contact electrodes 2 arranged in the form of a matrix 3. The electrodes 2 are adapted to be integrated with a bed 4 or the like. For this purpose the electrodes 2 are preferably made as electrode structures on a flexible substrate to be integrated with the bed 2 (e.g. by evaporating an electrode structure using a flexible foil) or the electrodes 2 may even be woven into a bedsheet or the like in order to form the matrix 3. Each electrode 2 is individually selectable for carrying out a capacitive measurement by means of a control unit 5. The control unit 5 is connected to all electrodes 2 via a number of connecting lines (not shown).

If a patient (not shown) is positioned on the bed 3, the system 1 is adapted to find out the most suitable electrodes 2 for carrying out the intended capacitive measurement.

According to a first embodiment of the invention, the position of the patient is determined, as schematically illustrated in FIG. 2. Depending on the position of the patient a number of electrodes facing the patient are stressed by the patient. For illustration purposes four adjacent electrode pairs are depicted in FIG. 2, each electrode pair comprising an electrode (counter electrode) 6 facing the patient and a sensing electrode 7. The electrode 6' facing the patient of one electrode pair within the matrix 3 is stressed by e.g. a patient's leg (illustrated by a number of arrows directed towards the electrode 6'). A dielectric 8, which is positioned between the electrode 6' facing the patient and the sensing electrode 7' concerned, is compressed and the capacitance of this electrode pair changes. This change of capacitance is detected by a bridge circuit of an analyzing unit. The analyzing unit is provided as an integral part of the control unit 5.

According to a second embodiment of the invention, as shown in FIG. 3, the body 9 of the patient is used as a "counter electrode" and the patient now directly pushes down the dielectric 8. Again the change of capacitance is detected by a bridge circuit of the analyzing unit, which again is part of the control unit 5.

According to a third embodiment of the invention, the arrangement as shown in FIG. 3 is modified. For this purpose a voltage signal is supplied to an electrode 10 and an induced charge is determined at an adjacent electrode 11. This embodiment is illustrated in FIG. 4. The voltage signal is supplied to the electrode 10 by the control unit 5 through the connecting line and the determination of the induced charge is preferably carried out using a charge amplifier (not shown). Some of these components, e.g. electrical circuits, may be placed near the electrodes 10, 11 or even integrated with an electrode. In other words, components may be integrated with the matrix 3, i.e. included in the bedsheet or bed 2. The control unit 5 is adapted to address each electrode 10, 11 separately.

From the measured charge the capacitance between the two electrodes 10, 11 is determined by means of the analyzing unit. This capacitance also depends on the position of the patient, which may be positioned at a certain distance to the sensing electrode 11. Thus, even if the patient is not in direct contact with an electrode, the patient's position may influence the measuring results. Since all parameters of the transmitted voltage signal are known, the sensitivity of the sensing electrode 11 can be "calibrated" in order to filter out parasitic signals during the subsequent real ECG measurement. Preferably a large number or even all electrodes are tested in this way prior to carrying out the real measurements. Thus the electrodes that show the best performance, e.g. in terms of signal coupling, can be determined.

This measuring arrangement can also be used for determining electrically induced charges due to the patient's heart beat during a subsequent measurement. Measuring the heart rate of the patient in this way may by carried out alternatively or simultaneously to the active measurements of the capacitance changes due to the presence of the (conductive) body of the patient. Electrode structure and electronics preferably provide a high input impedance, typically $10^{13}$ Ohm at 1 Hz in order to allow for remote sensing of electrical potentials and measure a contactless ECG signal. In other words, with the present invention a measuring procedure is provided, during which the electrode sensitivity can be calibrated using the changes in capacitance due to the presence of a conductive human body. Additionally the measuring procedure allows quantitative evaluation of body impedance. With the same calibration method the validity of ECG signals can be evaluated.

According to a fourth embodiment of the invention the system 1 comprises a shielding 12 of the conductive paths. The shielding structure is adapted in a way that openings 13 are provided in the active measurement regions above the electrodes 2, whereas shielding material is used to embrace the openings 13. In case a measuring arrangement is used without counter electrodes 6, the shielding 12 is preferably provided as shielding layer positioned on the side of the dielectric 8 facing the patient, as illustrated in FIG. 5.

Preferably an electrode testing procedure as described above is carried out for all electrodes 2 arranged within the matrix 3. From the capacitance values of each electrode 2 the exact position of the patient is determined by means of the analyzing unit. If suitable electrodes 2 have been determined and (pre)selected, the real capacitive ECG measurement is performed. The process of selecting suitable electrodes 2 may include a preselection (according to the parameters described above) as well as a final selection, preferably taking into account the kind of measurement. For example, if a ECG measurement is to be carried out, the electrodes 2 to be finally selected need to have a certain mutual distance. From the position data it is even possible to determine the location of the patient's extremities. Thus electrodes 2 can preferably be selected according to their position relative to suitable measuring points of the patient's body, e.g. the lower end of an arm or the middle of the thorax.

The system 1 with a sensor arrangement as described above can also be used for bio-impedance measurements. In this case preferably four suitable electrodes have to be determined. Two electrodes are used for inducing a current in the body to be probed. The other two electrodes show a potential difference depending on the impedance of the probed body. The analysis of the electrical parameters of the capacitive-resistive network allow a derivation of the tissue content. In the thoracic region this can help to identify water in the lungs of a patient. An analysis of body fat is also possible.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects to be illustrative and not restrictive, the scope of the invention being indicated by the appended claims rather than by the foregoing description, and all changes which come within the meaning and range of equivalency of the claims are therefore intended to be embraced therein. It will furthermore be evident that the word "comprising" does not exclude other elements or steps, that the word "a" or "an" does not exclude a plurality, and that a single element, such as a computer system or another unit may fulfill the functions of several means recited in the claims. Any reference signs in the claims shall not be construed as limiting the claim concerned.

REFERENCE NUMBER LIST 1 system
2 electrode
3 matrix
4 bed
5 control unit
6 counter electrode
7 sensing electrode
8 dielectric
9 patient's body
10 electrode
11 electrode
12 shielding
13 opening

The invention claimed is:

1. A patient monitoring system for monitoring cardio pulmonary performance by means of capacitive measurement, said system comprising:
a plurality of electrodes arranged in the form of a matrix, the plurality of electrodes being adapted to be integrated with a bed, each electrode of the plurality of electrodes being individually selectable to perform a capacitive measurement, wherein a sensitivity of each electrode of the plurality of electrodes in the matrix is calibrated to filter out parasitic signals from measured cardiopulmonary electrical signals,
a dielectric comprised of an elastic composition, the dielectric having a first side facing the plurality of electrodes and a second side on which one or more counter electrodes are arranged, the second side being opposite the first side, wherein a stress is detected in the dielectric if a patient is situated on the bed, the stress affecting a capacitance between an electrode of the plurality of electrodes and the one or more counter electrodes, and
a computer system programmed by computer-readable instructions that, when executed, cause the computer system to:
determine a capacitance between each electrode of the plurality of electrodes and the one or more counter electrodes;
determine suitable electrodes from the plurality of electrodes based on increases in the capacitances between each electrode of the plurality of electrodes and the one or more counter electrodes;
select a subset of the suitable electrodes for cardio pulmonary performance monitoring, wherein the selection is based on a suitable electrode being within a predetermined distance from at least one other suitable electrode, the selected subset of the suitable electrodes comprising two or more electrodes; and
monitor, via the selected subset of the suitable electrodes, cardio pulmonary performance of the patient, wherein the monitoring comprises one or more of electrocardiogram-based monitoring, electromyogram-based monitoring, electroencephalogram-based monitoring, or bio-impedance measurement-based monitoring.

2. The patient monitoring system as claimed in claim 1, wherein the computer system is further caused to detect, with a bridge circuit, the increases in the capacitances between each electrode of the plurality of electrodes and the one or more counter electrodes.

3. The patient monitoring system as claimed in claim 1, wherein determining the capacitance comprises:
supplying, with a voltage supply, a voltage signal to the plurality of electrodes.

4. The patient monitoring system as claimed in claim 1, comprising a shielding adapted to be located between the patient and the dielectric.

5. The patient monitoring system as claimed in claim 1, wherein (i) the body of the patient or (ii) an object placed on the dielectric acts as the one or more counter electrodes.

6. The patient monitoring system as claimed in claim 1, wherein the dielectric comprises a textile bed sheet.

7. The patient monitoring system as claimed in claim 1, wherein responsive to the patient being situated on the bed, a distance between an electrode of the plurality of electrodes and the one or more counter electrodes is reduced thereby causing an increase in the capacitance between the electrode of the plurality of electrodes and the one or more counter electrodes.

8. A method for monitoring cardio pulmonary performance by means of a capacitive measurement with a system, the system comprising one or more processors, said method comprising the steps of:
    arranging a plurality of electrodes in the form of a matrix, the plurality of electrodes being adapted to be integrated with a bed, each electrode of the plurality of electrodes being individually selectable to perform a capacitive measurement,
    disposing a dielectric comprised of an elastic composition, the dielectric having a first side facing the plurality of electrodes and a second side on which one or more counter electrodes are arranged, the second side being opposite the first side, wherein a stress is detected in the dielectric if a patient is situated on the bed, the stress affecting a capacitance between an electrode of the plurality of electrodes and the one or more counter electrodes,
    supplying, with a voltage supply, a voltage signal to the plurality of electrodes to determine a capacitance between each electrode of the plurality of electrodes and the one or more counter electrodes,
    determining, with the one or more processors, suitable electrodes from the plurality of electrodes based on increases in the capacitances between each electrode of the plurality of electrodes and the counter electrode,
    filtering, with the one or more processors, out parasitic signals from measured cardiopulmonary electrical signals by calibrating a sensitivity of each electrode of the suitable electrodes
    selecting, with the one or more processors, a subset of the suitable electrodes for cardio pulmonary performance monitoring, wherein the selection is based on a suitable electrode being within a predetermined distance from at least one other suitable electrode, the selected subset of the suitable electrodes comprising two or more electrodes; and
    monitoring, with the selected subset of the suitable electrodes, cardio pulmonary performance of the patient, wherein the monitoring comprises one or more of electrocardiogram-based monitoring, electromyogram-based monitoring, electroencephalogram-based monitoring, or bio-impedance measurement-based monitoring.

9. The method of claim 8, wherein the dielectric comprises a textile bed sheet.

10. The method of claim 8, wherein responsive to the patient being situated on the bed, a distance between an electrode of the plurality of electrodes and the one or more counter electrodes is reduced thereby causing an increase in the capacitance between the electrode of the plurality of electrodes and the one or more counter electrodes.

11. A patient monitoring system comprising:
    a plurality of electrodes arranged for forming a matrix, each electrode being individually selectable to perform a capacitive measurement, wherein a sensitivity of each electrode in the matrix is calibrated to filter out parasitic signals from measured cardiopulmonary electrical signals;
    a dielectric comprised of an elastic composition, the dielectric having a first side facing the plurality of electrodes and a second side on which one or more counter electrodes are arranged, the second side being opposite the first side,
    wherein a stress is detected in the dielectric if a patient is situated on the dielectric, the stress affecting a capacitance between an electrode of the plurality of electrodes and the one or more counter electrodes, and
    a computer system programmed by computer-readable instructions that, when executed, cause the computer system to:
        determine a capacitance between each electrode of the plurality of electrodes and the one or more counter electrodes;
        determine suitable electrodes from the plurality of electrodes based on increases in the capacitances between each electrode of the plurality of electrodes and the counter electrode; and
        select a subset of the suitable electrodes for cardio pulmonary performance monitoring, wherein the selection is based on a suitable electrode being within a predetermined distance from at least one other suitable electrode, the selected subset of the suitable electrodes comprising two or more electrode wherein the cardio pulmonary performance monitoring comprises one or more of electrocardiogram-based monitoring, electromyogram-based monitoring, electroencephalogram-based monitoring, or bio-impedance measurement-based monitoring.

12. The patient monitoring system of claim 11, wherein the plurality of electrodes are integrated as part of a bed.

13. The patient monitoring system of claim 11, wherein the computer system is further caused to detect, with a bridge circuit, the increases in the capacitances between each electrode of the plurality of electrodes and the one or more counter electrode.

14. The patient monitoring system of claim 11, further comprising:
    a voltage supply that supplies a voltage signal to the plurality of electrodes to determine a capacitance between each electrode of the plurality of electrodes and the one or more counter electrodes.

15. The patient monitoring system of claim 11, further comprising a shielding adapted to be located between the patient and the dielectric.

16. The patient monitoring system of claim 11, wherein the dielectric comprises a textile bed sheet.

17. The patient monitoring system of claim 11, wherein responsive to the patient being situated on the bed, a distance between an electrode of the plurality of electrodes and the one or more counter electrode, is reduced thereby causing an increase in the capacitance between the electrode of the plurality of electrodes and the one or more counter electrodes.

* * * * *